May 31, 1949. R. L. BYRUM Plant Pat. 844
ROSE PLANT
Filed Oct. 3, 1947
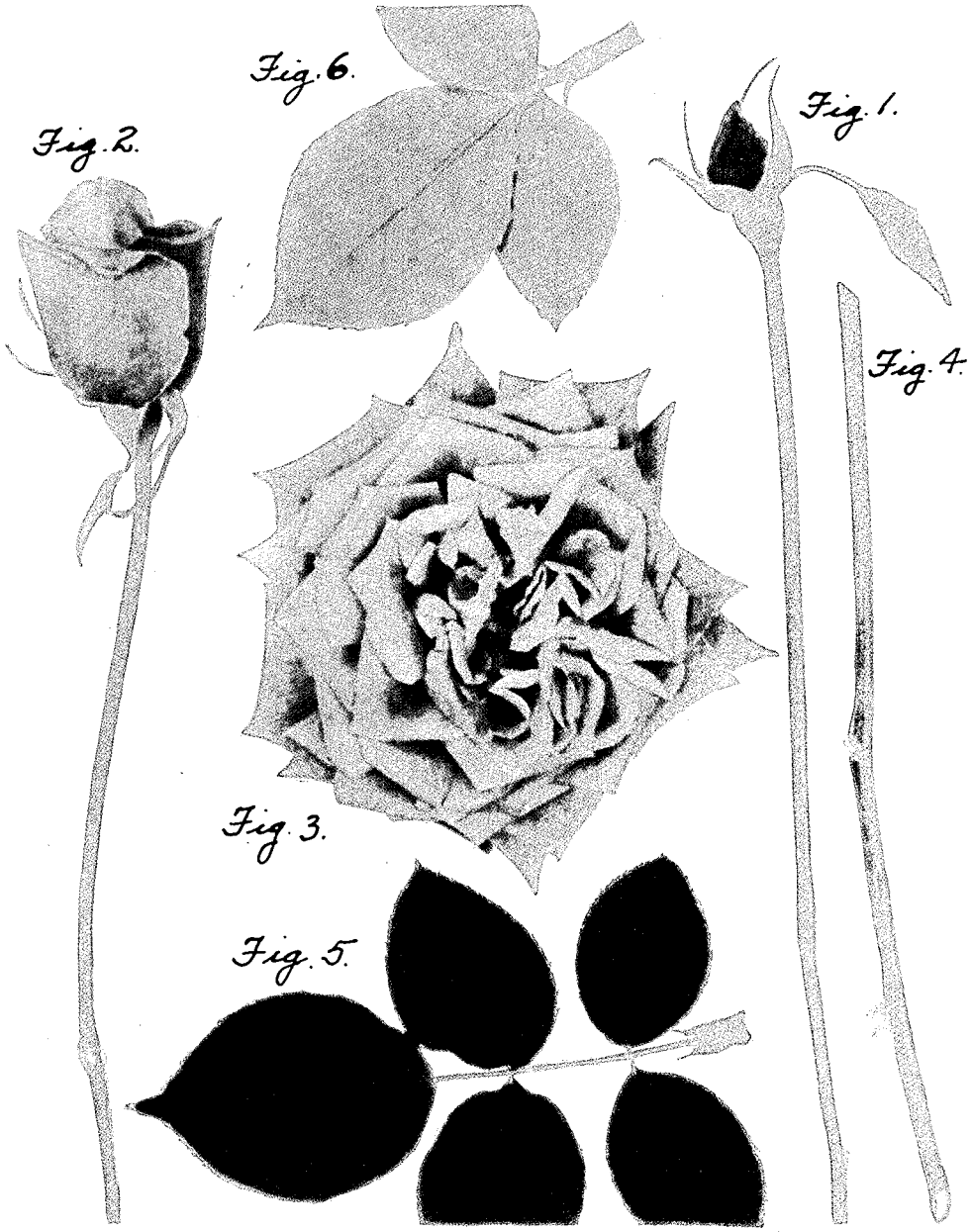
Inventor:
R. L. Byrum
By: Robb & Robb
Attorneys.

Patented May 31, 1949

Plant Pat. 844

UNITED STATES PATENT OFFICE

844

ROSE PLANT

Roy L. Byrum, Richmond, Ind., assignor to Joseph H. Hill Company, Richmond, Ind., a corporation of Indiana Application October 3, 1947, Serial No. 777,713

1 Claim. (Cl. 47—61)

The present invention relates to a new and distinct variety of rose plant, the result of a definite effort to improve primarily upon the color of the flowers of one of its parents while retaining the good qualities of said parent.

In carrying out this objective, I selected as the pollen parent a seedling (unpatented) which produced extra large blooms and good healthy growth. This seedling had the good qualities which were desirable for a rose suitable for greenhouse uses, but the red color of its blooms was not satisfactory. Therefore, I chose as the seed parent for this cross a seedling (also unpatented) which produced large, dark pink flowers, with the expectancy that the brilliancy of the pink would be added to the red and the cross thus result in a brilliant red color.

As will be seen from the accompanying illustration, I succeeded in not only obtaining the improvement in color of the flowers, but a variety possessing the combination of characteristics of good, free growth, large size and brilliant deep red flowers, particularly suited for greenhouse uses, as well as others.

Asexual reproduction shows that the characteristics hold true through succeeding propagations.

In the drawings:

Fig. 1 shows a specimen of single stem and flower in the bud stage, as the calyx breaks;

Fig. 2 shows a specimen of flower as the petals first open;

Fig. 3 illustrates a full blown flower, its large size, large number, form and arrangement of its petals and petaloids;

Fig. 4 shows a section of a branch illustrating the characteristics of the thorns;

Fig. 5 shows the upper dark green surface of a specimen of the foliage; and

Fig. 6 shows the light green under surface of the foliage.

The following is a more detailed description of this new variety, color terminology being in accordance with Ridgway's Color Standards and Nomenclature, except where otherwise indicated by ordinary dictionary definitions:

Type: Tall; bush; greenhouse; seedling; for cut flowers.

Class: Hybrid tea.

Breeding: Seedling.

*Seed parent.*—Unnamed (large dark pink flowers) seedling.

*Pollen parent.*—Unnamed (large red flowers) seedling.

Propagation: Holds its distinguishing characteristics through succeeding propagations by cutting, grafting and budding. Layering not yet tried.

*Flower*

Locality where grown: Richmond, Indiana.

Flowers borne: Singly to stem, on strong, long stems.

Quantity of bloom: Free; in greenhouse.

Continuity: Continuous.

Fragrance: Moderate tea.

Bud:

*Peduncle.*—Long; heavy; slightly bending; medium green; almost smooth; few yellow hairs.

*Before calyx breaks.*—*Size*—large. *Form*—short, pointed, with a conspicuous neck; with foliaceous appendages on the surface of the bud; with foliaceous parts extending beyond the tip of the bud equal to one-half or more of its length.

*As calyx breaks.*—Oxblood Red, Plate 1, washed with Victoria Lake, Plate 1.

*As first petal opens.*—*Size*—large. *Form*—short, pointed. *Color*—outside: Carmine, Plate 1, washed with Oxblood Red, Plate 1; inside: Spectrum Red, Plate 1, overlaid with a velvety Carmine, Plate 1.

*Openings.*—Opens up well.

Bloom: Size, when fully open, very large; 3½ to 4½ inches.

*Petalage.*—Very double; from 50 to 55 petals arranged irregularly.

*Form.*—Full, high center at first, becoming open; petals remaining at first very tightly rolled outward; becoming later, at maturity, loosely rolled outward.

Petals: Thick; satiny.

*Shape.*—Outside, intermediate and inside—obovate.

This description of a newly opened flower was made from a rose grown in a greenhouse in the month of November, at Richmond, Indiana:

*Color.* — Outside petal — outside surface: Carmine, Plate 1, blotched with Oxblood Red, Plate 1; inside surface: Velvety Red, between Spectrum Red, Plate 1, and Carmine, Plate 1. *Intermediate petal*—outside surface: same as outside surface of outside petal; inside surface: same as inside surface of outside petal but not as velvety. *Inner petal*—outside surface: same as outside surface of intermediate petal; inside surface: same as inside surface of intermediate petal.

This description was made from a rose that was open for three days in a greenhouse in the month of November, at Richmond, Indiana:

*Color.*—Lighter than newly opened flower.

*General color effect.*—Newly opened flower—Carmine, Plate 1. Three days open—between Carmine, Plate 1, and Spectrum Red, Plate 1.

*Behavior.*—Persist.

*Flower longevity.*—Cut roses grown in greenhouse kept at living room temperatures—four to five days in November.

*Reproductive Organs*

Stamens: Medium number arranged regularly about pistils; tucked in calyx.

Filaments: Short; reddish; most with anthers.

Anthers: Medium size; reddish brown; all open at once.

Pollen: Moderate; gold.

Pistils: Medium number.

Styles: Uneven; short; medium heavy; bunched.

Stigma: White.

Ovaries: All enclosed in calyx.

Sepals: Permanent; moderately long; spear-shaped, curled. *Color*—inside: Light Cress Green, Plate XXXI, with white fuzz; outside: Cress Green, Plate XXXI.

*Plant*

Foliage:

*Leaves.*—Compound of five leaflets; abundant; very large; leathery.

*Leaflets.*—Ovoid with apex obtuse; base round; margin simply serrate.

*Color.*—*Mature*—upper surface: dark green; under surface: light green. *Young*—upper surface: light bronze red; under surface: moderately bronze red.

*Rachis.*—Medium heavy. Upper side—grooved; under side—hairy.

*Stipules.*—Medium long; narrow; moderately long points, turning out at an angle of less than 45°.

*Disease.*—Resistant to mildew and blackspot.

Growth:

*Habit.*—Bush; upright; branched.

*Growth.*—Vigorous.

*Canes.*—Heavy.

*Main stems.*—Dull green. *Thorns*—few; medium length; hooked downward; with short, narrow base. *Prickles and hairs*—none.

*Branches.*—Bright green. *Thorns*—few; medium length; hooked downward; with short, narrow base. *Prickles and hairs*—none.

*New shoots.*—Dull bronze. *Thorns*—few; short; hooked downward; with short, narrow base. *Prickles and hairs*—none.

I claim:

A new and distinct variety of hybrid tea rose plant, characterized as to novelty by its habit of growth; its extra large size flowers of deep brilliant red; and qualities especially suitable for greenhouse purposes, substantially as shown and described.

ROY L. BYRUM.

No references cited.